US012599351B2

(12) United States Patent
　　Roser

(10) Patent No.:　US 12,599,351 B2
(45) Date of Patent:　　Apr. 14, 2026

(54) IMAGING HAVING SCATTER CORRECTION BY INTERPOLATION

(71) Applicant: Siemens Healthineers AG, Forchheim (DE)

(72) Inventor: Philipp Roser, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 240 days.

(21) Appl. No.: 18/418,173

(22) Filed: Jan. 19, 2024

(65) Prior Publication Data

US 2024/0245378 A1　　Jul. 25, 2024

(30) Foreign Application Priority Data

Jan. 20, 2023　(DE) ..................... 10 2023 200 426.7

(51) Int. Cl.
G06N 3/08　　　　　(2023.01)
A61B 6/00　　　　　(2006.01)

(52) U.S. Cl.
CPC .......... A61B 6/5205 (2013.01); A61B 6/4441 (2013.01); A61B 6/5223 (2013.01); A61B 6/5282 (2013.01); G06N 3/08 (2013.01)

(58) Field of Classification Search
CPC ....... G06F 18/214; G06F 18/217; G06N 3/08; G06V 10/751; G06V 10/7715; G06V 10/82; G06V 10/993; G06V 2201/03; G06V 20/698; G06T 11/005; G06T 11/008; G06T 2207/20081; G06T 15/00; G06T 17/00; A61B 6/5282; A61B 6/5205; A61B 6/5235
See application file for complete search history.

(56) References Cited

U.S. PATENT DOCUMENTS

| | | | |
|---|---|---|---|
| 2018/0078221 A1 | 3/2018 | Petersilka | |
| 2020/0302297 A1* | 9/2020 | Jaganathan | ............. G06F 16/58 |
| 2021/0121149 A1 | 4/2021 | Manhart | |
| 2021/0330274 A1 | 10/2021 | Birkhold | |

FOREIGN PATENT DOCUMENTS

| | | |
|---|---|---|
| DE | 102016217984 A1 | 4/2018 |
| DE | 102019216329 A1 | 4/2021 |

OTHER PUBLICATIONS

Maier, Joscha, et al. "Real-time scatter estimation for medical CT using the deep scatter estimation: method and robustness analysis with respect to different anatomies, dose levels, tube voltages, and data truncation." Medical physics 46.1 (2019): 238-249.

* cited by examiner

*Primary Examiner* — Don K Wong

(74) *Attorney, Agent, or Firm* — Lempia Summerfield Katz LLC

(57) ABSTRACT

In order to reduce a computing effort for correcting initial images from an imaging apparatus, a scatter model is used to simulate scattered-radiation images, and corresponding initial images are selected from the original initial images. These are used to train a neural network. The neural network may be used to calculate scattered-radiation single images that may be used to correct each individual initial image into a corrected initial image.

15 Claims, 2 Drawing Sheets

FIG 1

IMAGING HAVING SCATTER CORRECTION BY INTERPOLATION

This application claims the benefit of German Patent Application No. DE 10 2023 200 426.7, filed on Jan. 20, 2023, which is hereby incorporated by reference in its entirety.

BACKGROUND

The present embodiments relate to training a neural network for correcting acquisitions obtained by an imaging apparatus, correcting acquisitions obtained by radiation, a corresponding imaging system, and to a computer program.

Modern imaging methods (e.g., X-ray based imaging methods, such as fluoroscopy methods) are sometimes used to assist in interventions. In these cases, an instrument inserted or introduced into the object under examination, or another device, may be imaged and tracked inside the object (e.g., in a vessel structure of the object) during the intervention.

It is desirable to achieve the highest possible image quality in order to be able to track the device as accurately as possible in relation to the vessel structure and hence to be able to guide the device as precisely as possible inside the object. For example, in the context of X-ray based imaging methods, it may be difficult to identify the device clearly and to distinguish the device clearly from other elements of the image (e.g., depictions of tissue structures or bone structures or even the vessel structure). The same applies to the identifiability of the vessel structure with respect to other tissue or the like.

Scattered X-ray photons play an important role in the image quality of, for example, cone-beam computed tomography (CBCT). Without suitable compensation, scattered rays drastically reduce the achievable image quality and lead to streaking, cupping (e.g., elevation in the center), and smearing artifacts, which may lead to an incorrect diagnosis or treatment. Therefore, today's commercial CBCT-capable systems use an antiscatter grid in front of the detector, which physically blocks the incident X-rays. This grid also has disadvantageous effects, however. First, the grid also blocks some of the incident primary radiation, which may increase the applied dose (e.g., because of automatic readjustment). Second, for 2D image quality, a better image quality and lower dose may be achieved if the antiscatter grid is removed, relying solely on what is known as the air-gap technique. This applies especially for neurovascular interventions in the brain (e.g., when treating aneurysms or embolic strokes). In order to avoid the antiscatter grid, a special software solution for scatter compensation is desirable in CBCT imaging.

Methods based on "deep learning" have been proposed recently for compensating for scatter in the projection region (Maier, J., Eulig, E., Vöth, T., Knaup, M., Kuntz, J., Sawall, S. and Kachelrieβ, M. (2019), Real-time scatter estimation for medical CT using the deep scatter estimation: Method and robustness analysis with respect to different anatomies, dose levels, tube voltages, and data truncation. Med. Phys., 46: 238-249. https://doi.org/10.1002/mp.13274). While these methods are extremely fast, their general robustness is problematic because of their dependency on the training data. This dependency provides that it is difficult to cover all possible combinations of X-ray physics, collimation, focal spot size, and so on in a combined training cohort. Further, such methods may only be trained using simulated pairs of input and output data, resulting in a considerable gap between simulation and reality.

The de facto gold standard is to simulate the X-ray physics either by solving the Boltzmann transport equation directly and deterministically or by approximating the image generation stochastically using Monte Carlo methods. While these methods deliver highly accurate results, their use in the interventional setting is problematic because of their inherent high computational complexity.

The same applies to what are known as empirical methods, which estimate and optimize the X-ray scatter based on an image quality metric in the reconstructed image slices. These methods contain numerous reconstruction steps, likewise resulting in high computational complexity.

Document US 2021/0330274 A1 discloses a computer-implemented method for correcting X-ray image data with regard to noise effects. A statistical physical model, which is parameterized by model parameters, is used to describe the noise effects.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an improved concept for imaging, such as for X-ray based imaging, by which it is possible to achieve high image quality with reduced computational complexity, is provided.

According to the present embodiments, a method is provided for training a neural network for correcting acquisitions obtained by an imaging apparatus. The imaging apparatus may be an X-ray imaging apparatus, for example, in which the acquisitions are obtained by X-ray radiation. For example, this may be a C-arm device or a computed tomography (CT) device.

In a first method act of the method according to the present embodiments, a plurality of initial images are acquired at different acquisition coordinates by the imaging apparatus (e.g., acquisitions are obtained). The subsequent image processing is based on these initial images. Different acquisition coordinates of the imaging apparatus are used for acquiring these initial images. For example, the acquisitions are obtained from different angles with respect to the object to be acquired. In this case, the angular coordinate forms the corresponding acquisition coordinate. The acquisition coordinates may also be linear coordinates or other coordinates, however.

In a further act of the method according to the present embodiments, a number of simulated scattered-radiation images are obtained from the plurality of initial images using a scatter model. The number of simulated scattered-radiation images is less than the plurality of initial images, with each simulated scattered-radiation image being assigned at least one corresponding acquisition coordinate. Thus, scattered-radiation images are obtained by simulation from the previously acquired initial images. A reduced number of scattered-radiation images compared with the plurality of initial images are obtained or simulated in this process rather than the same number of scattered-radiation images. This reduces the simulation effort. If, for example, 500 projection images or initial images are acquired, then, for example, only ten scattered-radiation images are simulated by the scatter model. The number of scattered-radiation images may be less than the number of initial images by a factor of 2, 3, and so on (e.g., by at least an order of magnitude). The simulation may be performed by a Monte Carlo method or by a deterministic calculation. Each simulated scattered-radiation image is assigned at least one corresponding acquisition coordinate. For example, a simulated scattered-radiation image is assigned an acquisition angle of a C-arm device as the acquisition coordinate. This coordinate is used in the scatter model to give the angle of incidence of the radiation onto the object under examination, for example.

In a further act, those images of the plurality of initial images that have respective acquisition coordinates equal to those of the simulated scattered-radiation images are selected. Thus, pairs of simulated scattered-radiation images and actually acquired initial images may be produced based on the acquisition coordinates. The number of pairs equals the number of simulated scattered-radiation images and hence is less than (e.g., considerably less than) the number, or plurality, of initial images.

A neural network is trained using the selected initial images as input data and the simulated scattered-radiation images as output data. Thus, the neural network is trained using the reduced number of initial images and the associated scattered-radiation images. For this purpose, in practice, the selected initial images form what is known as the input layer, and the simulated scattered-radiation images form what is known as the output layer. Thus, the neural network is trained based on a reduced number of pairs of actually acquired initial images and simulated scattered-radiation images. This may achieve a lower computational effort.

It is provided in an embodiment that, for obtaining the simulated scattered-radiation images, an uncorrected 3D image is reconstructed from the plurality of initial images, and the simulated scattered-radiation images are obtained from the uncorrected 3D image by simulation. Thus, initially, an uncorrected 3D image of the object to be imaged is created from the uncorrected initial images. This uncorrected 3D image is the basis for the simulation of the scattered-radiation images. Alternatively, the simulation may also be carried out based on the initial images without the intermediate step of reconstructing a 3D image. The reconstructed 3D image has the advantage, however, that further simulated scattered-radiation images may be obtained without additional effort.

In a further embodiment, the imaging apparatus is an X-ray apparatus and, for example, a C-arm device that is used to obtain the initial images. The imaging apparatus is thus based on X-ray technology. The imaging modality may therefore be configured, for example, as an X-ray imaging modality (e.g., a digital X-ray image device, such as a C-arm X-ray imaging modality; a C-arm device). In this case, the imaging modality contains, for example, an X-ray source and a sensor unit. The sensor unit may contain, for example, a detector array (e.g., a two-dimensional detector array) of optical detectors (e.g., photodiodes) that may produce the at least one sensor dataset.

In the embodiment having the C-arm device, the simulated scattered-radiation images may be evenly distributed in terms of the acquisition coordinates over an acquisition region of the C-arm device. If, for example, an acquisition region of 200 degrees is selected for the C-arm device, then one scattered-radiation image may be simulated for every 20 degrees, for example. This may result in eleven simulated scattered-radiation images for the ten intervals, including a first scattered-radiation image and a final scattered-radiation image. The even distribution may also be based on a different number, however, and is not limited to ten. Alternatively, it is also possible to depart from an even distribution, for example, if it is found that the scattered radiation varies particularly strongly in a certain angle range. In this case, for example, more simulations may be carried out for this intensified variation region than in other regions.

In an embodiment, the acquisition region of the C-arm device is greater than 180 degrees, and the number of simulated scattered-radiation images is less than 30 (e.g., is less than 20). In addition, typically several hundred initial images (e.g., 500) are obtained over an acquisition region of 180 degrees. Thus, for the training, a scattered-radiation image is simulated only for every 25th initial image, for example. The training may therefore be carried out significantly faster that in the case of the training being carried out with all the initial images and associated scattered-radiation images.

In a further embodiment, the neural network is calibrated by a physical model before the training. The calibration may be performed as in the above-mentioned document US 2021/0330274 A1, for example. This pre-calibration provides that the training does not have to start completely at zero. Instead, the individual weights of the neural network are already given a meaningful initial setting based on the physical circumstances (e.g., the nature of the acquisition region, type of patient, X-ray dose, etc.).

Thus, according to the present embodiments, a method may be provided for correcting acquisitions obtained by radiation (e.g., X-ray radiation) by creating one scattered-radiation single image for each initial image using a neural network trained in accordance with the above method, and by correcting each initial image using the corresponding scattered-radiation single image. Thus, the neural network trained using a few simulated scattered-radiation images may be provided in order to estimate, for all the initial images, corresponding scattered-radiation images, so that all the initial images may be corrected by the respective scattered-radiation images. Hence, in order to generate, by the neural network, one individual scattered-radiation image for each of all the initial images, according to the present embodiments, it is only necessary to train the neural network with a smaller number of pairs of initial images and scattered-radiation images. Each initial image may be corrected, for example, by subtracting from an initial image the corresponding scattered-radiation image. If applicable, however, further processing of the scattered-radiation images (e.g., weighting or the like) may also be carried out for the correction.

According to an embodiment, the number of scattered-radiation images simulated for the training may be increased automatically until a specified accuracy is achieved with regard to pixel values relating to the acquisition coordinates of adjacent scattered-radiation single images. Accordingly, for example, if the pixel values of predefined pixels of adjacent scattered-radiation single images vary by more than a specified amount, this may be a sign of a neural network that is not sufficiently trained. Therefore, in this case, the number of training pairs of initial images and scattered-radiation images is increased. This increase may be performed successively until the pixel values of individual pixels of adjacent scattered-radiation images no longer differ from each other excessively (e.g., the error lies below a specified threshold).

In a further embodiment, a corrected 3D image is reconstructed from the corrected initial images. For example, the initial images from a C-arm sequence have been corrected in accordance with the method presented above, resulting in a reduction in the scattered-radiation effects in the individual images. These corrected individual images or initial images may now be the basis for the reconstruction of a 3D image in order to obtain a corrected 3D image in which the scattered-radiation effects are likewise correspondingly reduced.

Thus, according to the present embodiments, a method may be provided for obtaining acquisitions (e.g., X-ray acquisitions) of an object, during which a method as was described above is carried out. This provides, in practice, that intraoperative training of the neural network takes place. In other words, the neural network is being trained while X-ray acquisitions of the object are being obtained (e.g., as part of an intervention). Hence, it is not necessary to train the neural network, with additional exposure of the object to radiation, before the actual examination/monitoring. Instead, the training may be performed during an intervention, for example, because of the reduced computational effort for the training.

The object presented above is also achieved according to the present embodiments by an imaging system having an imaging apparatus and an image processing apparatus, which are configured to implement one of the above-mentioned methods. For example, the imaging system may have a control facility that is configured to train a neural network for correcting acquisitions obtained using the imaging apparatus. The imaging apparatus may be configured, for example, to acquire a plurality of initial images at different acquisition coordinates. The imaging apparatus may be configured to obtain a number of simulated scattered-radiation images from the plurality of initial images using a scattered-radiation model; the number is less than the plurality of initial images, with each simulated scattered-radiation image being assigned at least one corresponding acquisition coordinate. The imaging apparatus or its control facility may be configured, for example, to select those images of the plurality of the initial images that have respective acquisition coordinates equal to those of the simulated scattered-radiation images, and to train the neural network using the selected initial images as input data and the simulated scattered-radiation images as output data.

For cases of use or situations of use that may arise in the method and are not explicitly described here, it may be provided that, according to the method, an error message and/or a prompt to enter user feedback is output and/or a default setting and/or a predefined initial state is set.

Further embodiments of the imaging system according to the present embodiments follow from the various embodiments of the method according to the present embodiments, and vice versa. For example, the imaging system according to the present embodiments may be configured to perform a method in accordance with the improved training concept or correction concept according to the present embodiments.

In addition, a computer program (e.g., product) containing commands is defined in accordance with the improved concept according to the present embodiments. When the commands are executed by an imaging system according to the improved concept (e.g., by a control or computing unit of the imaging system), the commands cause the imaging system to perform a method in accordance with the improved concept.

The computer program product may be in the form of a computer program containing the commands. The computer program product may also be in the form of a computer-readable storage medium or electronically readable data storage medium that stores a computer program containing the commands.

The features and feature combinations mentioned above in the description, and the features and feature combinations mentioned below in the description of the figures and/or shown solely in the figures may be used not just in the particular combination stated but also in other combinations without departing from the scope of the invention. Further, embodiments and feature combinations that do not have all the features of an independent claim in the original wording and/or go beyond or differ from the feature combinations presented in the dependency references of the claims shall be deemed to be disclosed.

Independent of the grammatical term usage, individuals with male, female, or other gender identities are included within the term.

BRIEF DESCRIPTION OF THE DRAWINGS

FIG. 1 shows a schematic representation of an embodiment of an imaging apparatus;

DETAILED DESCRIPTION

Figure 1:
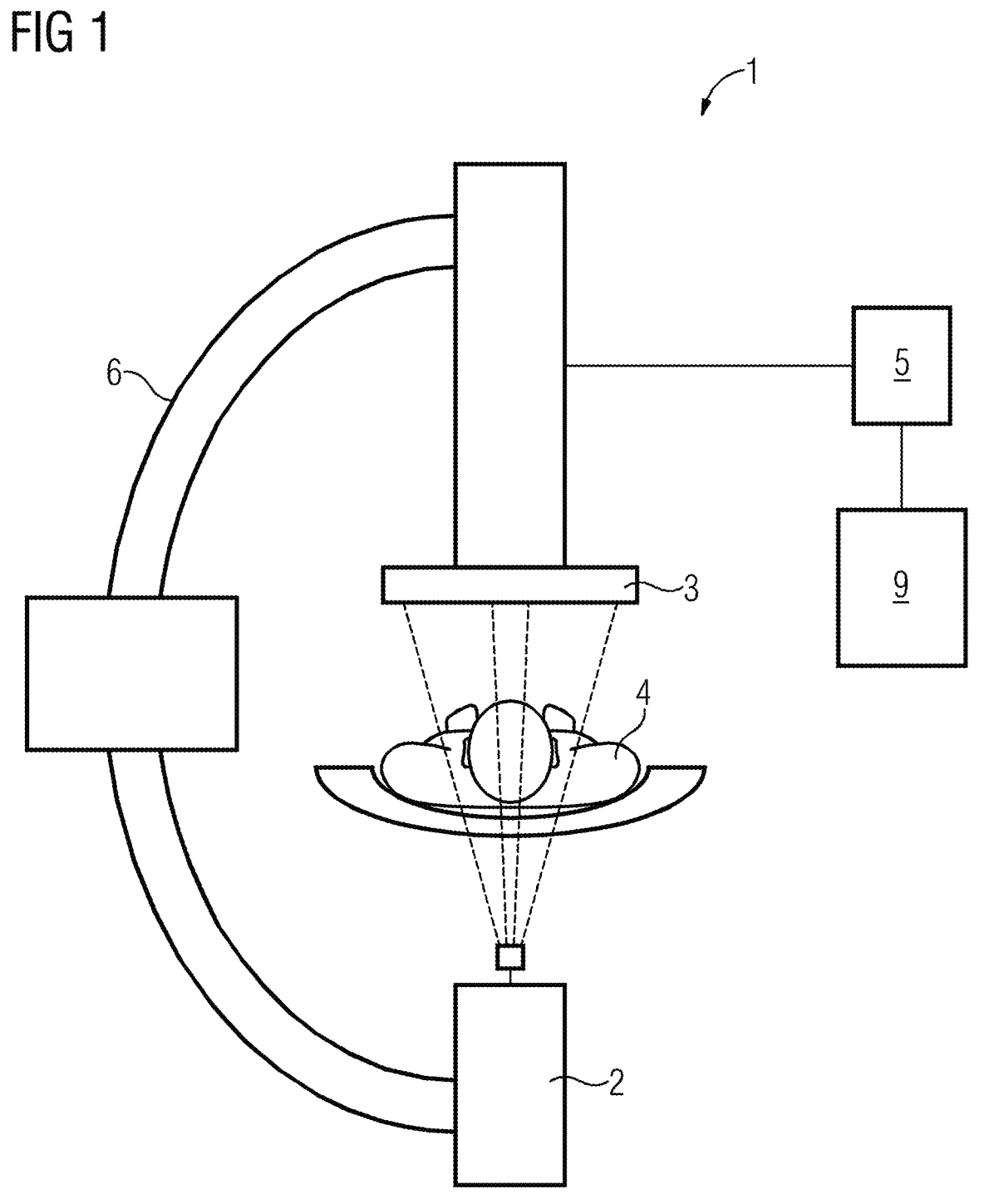
Figure 2:
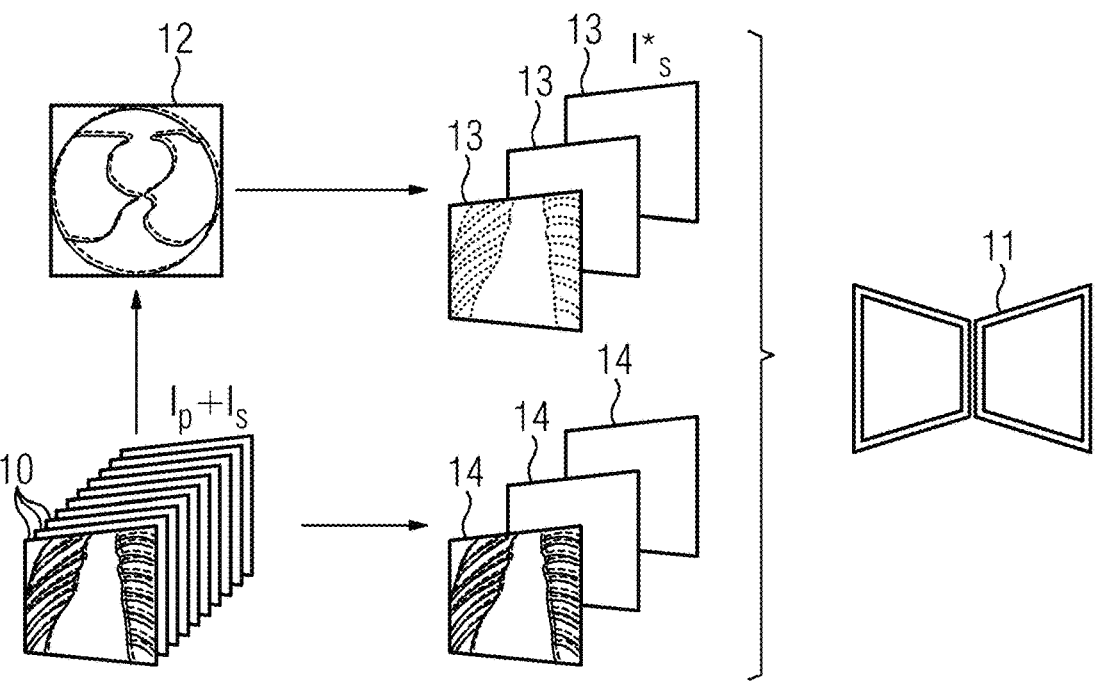
FIG. 2 shows a schematic visualization of an embodiment of a training method.

FIG. 1 shows schematically an embodiment of an imaging system 1 in the form of, for example, an X-ray imaging system. The example of FIG. 1 shows a design of the X-ray imaging system or device according to the principle of a C-arm device having a rotatable and movable C-arm 6 that may accordingly be turned and displaced in order to image from different directions (e.g., at different acquisition angles) an object 4 to be imaged. An imaging apparatus 1 according to the present embodiments may also have different structural designs, however. For example, the improved concept is not fundamentally restricted to X-ray based imaging methods.

Thus, the imaging apparatus 1 of FIG. 1 contains, by way of example, an X-ray source 2 that is configured to produce and emit X-ray radiation towards the object 4. A sensor 3 of the imaging apparatus is arranged on an opposite side of the object 4 from the X-ray source 2. The sensor 3 contains, for example, a detector array of photodiodes in order to be able to detect X-ray quanta passing through the object 4. The sensor 3 may then transmit the corresponding detector signals to a control or computing unit 5 of the imaging system 1 for further processing. The components 2 to 6 constitute an imaging apparatus that may transfer its images to an image processing apparatus 9. This may perform any corrections to the acquired images.

The imaging system 1 may be configured, for example, to carry out a rotational angiography method (e.g., based on the subtraction-angiography principle). In this case, the computing unit 5 may produce, for example, a number of two-dimensional projections (also referred to as initial images) acquired from different angles, and the computing unit 5 may calculate therefrom, if applicable, a three-dimensional reconstruction.

The manner of operation of the imaging system 1 is explained in greater detail below with reference to various embodiments of a training and/or correction method in accordance with the improved concept according to the present embodiments, in particular referring to the FIGS. 2 and 3.

Figure 3:
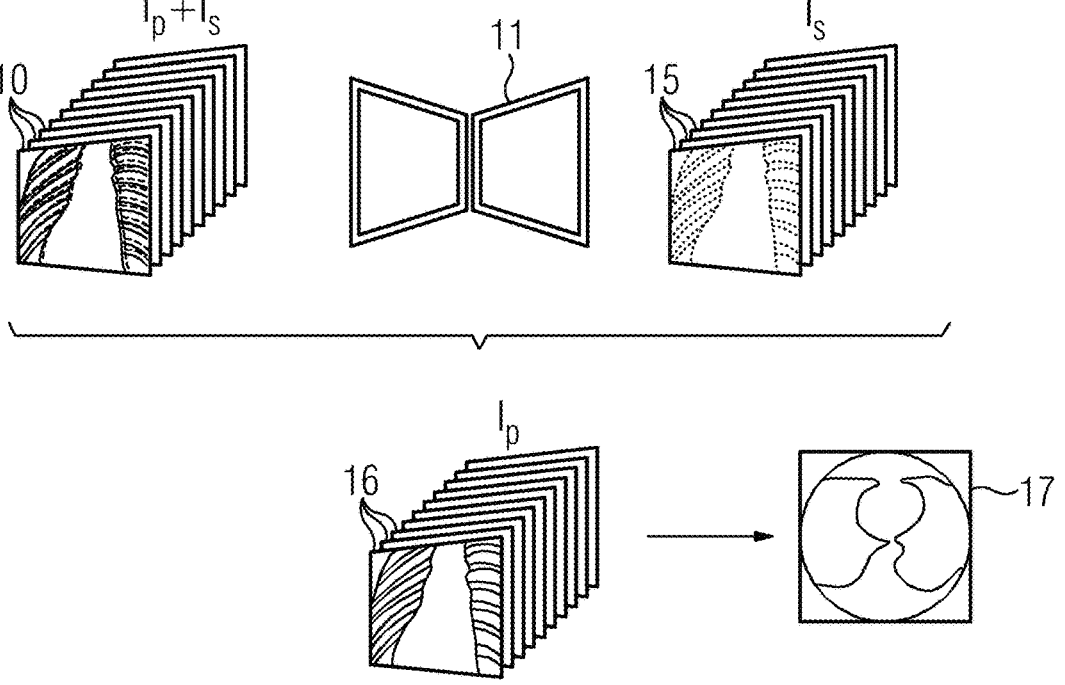
FIG. 3 shows a visualization of a correction method according to an embodiment.

The embodiment mentioned in connection with FIGS. 2 and 3 may be split into two sub-acts: a training method; and the actual correction method. The embodiment may be referred to overall as neural scatter interpolation (NSI). The embodiment exploits the advantages of deep-learning and simulation techniques, for example. Although is it generally known that deep learning models perform above average in the training cohort, this effect is rarely used specifically. NSI may be implemented as a purely interventional technique that does not depend on prior information.

The two sub-acts are presented in greater detail below. In the first sub-act, as shown in FIG. 2, the imaging apparatus 2 to 6 acquires a plurality of initial images 10. Each initial image 10 is acquired at a different angle by a C-arm, for example. In the present example, each initial image 10 constitutes an X-ray acquisition of a ribcage. Each individual initial image 10 is characterized by a primary intensity $I_p$ of the primary (X-ray) radiation and a secondary intensity $I_s$ of the secondary (X-ray) radiation. In each individual initial image 10, the two intensities $I_p$ and $I_s$ are initially superimposed. The aim is to remove the secondary intensity $I_s$ from each individual initial image 10. To achieve this, a neural network 11 is to be trained as shown in FIG. 2 in order to use this ultimately as shown in FIG. 3 for correcting the stack of initial images 10.

In the first sub-act, as shown in FIG. 2, a first, uncorrected, reconstruction 12 is optionally calculated using the entire stack of projections (e.g., initial images 10). Based on this uncorrected reconstruction 12, in coarse steps, a simulation of the scatter distribution that is obtained (e.g., evenly) along the acquisition trajectory (e.g., CBCT trajectory) is estimated. For example, the secondary or scatter intensity $I_s^*$ is estimated for every tenth acquisition position. This results in simulated scattered-radiation images 13 each having the estimated secondary intensity $I_s^*$. The simulation is performed using a scatter model based on the uncorrected reconstruction 12 or the stack of initial images 10, for example.

Experiments have shown that, for example, ten to twenty scatter simulations (e.g., simulated scattered-radiation images 13) are sufficient to cover the angle range of a short scan (e.g., 200 degrees).

The scattered-radiation images 13 are simulated for defined acquisition coordinates (e.g., acquisition angles) of the acquisition trajectory. The acquisition coordinates or the simulated scattered-radiation images 13 thereof may be distributed evenly over the acquisition trajectory. For the individual simulated scattered-radiation, images 13 are selected from the entire stack of initial images 10 (e.g., images that have the same acquisition coordinates as the simulated scattered-radiation images 13). This results in the selected initial images 14. The number of selected initial images 14 is less (e.g., substantially less) than the number of all acquired initial images 10. The number of simulated scattered-radiation images 13 equals the number of selected initial images 14.

The neural network 11 is now trained based on the simulations (e.g., the simulated scattered-radiation images 13) and the corresponding actually acquired projection images (e.g., the selected initial images 14). For the training, the selected initial images 14 serve as the input layer, and the simulated scattered-radiation images 13 serve as the output layer.

The architecture of the neural network may be selected freely, but a combination with a neural network informed by physical circumstances, as disclosed in document US 2021/0330274 A1, is recommended.

The training of the neural network 11 is a purely interventional or intraoperative technique and does not depend on prior information.

In the second sub-act, as shown in FIG. 3, the trained neural network 11 is now used to calculate one scattered-radiation single image 15 for each of all the initial images 10. Whereas the initial images 10 have the intensity $I_p+I_s$, the calculated scattered-radiation single images have the intensity or intensity distribution $I_s$. Hence, they represent the intensity distribution of the secondary radiation for the respective acquisition coordinates. The resultant scatter distributions of the individual scattered-radiation single images 15 may be used directly for correcting all the acquired projections or initial images 10. Correcting the original initial images 10 using the same number of scattered-radiation single images 15 results in corrected initial images 16 in the same number. The correction involves, for example, subtracting the corresponding scattered-radiation single image 15 from an initial image 10 in order to obtain an associated corrected initial image 16. The correction may be expressed as follows in terms of the intensity distribution: $(I_p+I_s)-I_s=I_p$. Hence, the associated specific scattered radiation is removed from each corrected initial image 16. A corrected 3D image 17 may now be reconstructed from the corrected initial images 16, which are equal in number to the original initial images. This corrected 3D image is free from scatter errors.

In an extended embodiment, it may be provided that the neural network 11 is pre-trained or initialized using a physical model, for example. This has the advantage that the neural network initialized in this way may be used already before the intraoperative training shown in FIG. 2.

According to another embodiment, an expected accuracy of the pixel values of the simulated scattered-radiation images 13 may be defined. If this accuracy cannot be achieved during the intraoperative training, additional simulations may be carried out until the accuracy is achieved. This provides that the number of simulated scattered-radiation images 13 is increased (e.g., automatically) until the desired accuracy is achieved. The approach according to the present embodiments provides that is it possible to combine an online simulation, training, and the productive use (e.g., inference) of the neural network within a single intervention method. This results in the following advantages. First, the computing complexity is reduced by a factor of up to fifty compared with approaches driven solely by simulation. Since the network is trained using, for example, only about ten datasets, the time taken for this is negligible, as is the effort to apply this training.

Second, the neural scatter interpolation (NSI) is intrinsically robust compared with pure deep learning methods. It is provided inherently that no data arises outside the distribution. Further, it is possible already while the network is being trained to monitor the expected accuracy based on the training data or potential additional validation data. If the expected accuracy does not satisfy a defined quality criterion, additional simulations may be carried out until the quality criterion is satisfied.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for training a neural network for correcting acquisitions obtained by an imaging apparatus, the method comprising:

acquiring a plurality of initial images at different acquisition coordinates using the imaging apparatus;

obtaining a number of simulated scattered-radiation images from the plurality of initial images using a scatter model, the number of simulated scattered-radiation images being less than the plurality of initial images, wherein each simulated scattered-radiation image of the number of simulated scattered-radiation images is assigned one corresponding acquisition coordinate;

selecting images of the plurality of initial images that have respective acquisition coordinates equal to acquisition coordinates of the number of simulated scattered-radiation images; and training the neural network using the selected images as input data and the number of simulated scattered-radiation images as output data.

2. The method of claim 1, wherein obtaining the number of simulated scattered-radiation images comprises:

reconstructing an uncorrected three-dimensional (3D) image from the plurality of initial images; and obtaining the number of simulated scattered-radiation images from the uncorrected 3D image by simulation.

3. The method of claim 1, wherein the imaging apparatus is an X-ray apparatus configured to obtain the plurality of initial images.

4. The method of claim 3, wherein the X-ray apparatus comprises a C-arm device.

5. The method of claim 4, wherein the number of simulated scattered-radiation images are evenly distributed in terms of the acquisition coordinates over an acquisition region of the C-arm device.

6. The method of claim 5, wherein the acquisition region of the C-arm device is greater than 180°, and the number of simulated scattered-radiation images is less than thirty.

7. The method of claim 6, wherein the number of simulated scattered-radiation images is less than twenty.

8. The method of claim 1, wherein the neural network is calibrated by a physical model before the training.

9. A method for correcting initial images obtained by radiation, the method comprising:

creating one scattered-radiation single image for each of the initial images using a neural network trained according to a method for training the neural network for correcting acquisitions obtained by an imaging apparatus, the method for training the neural network comprising:

acquiring a plurality of initial images at different acquisition coordinates using the imaging apparatus;

obtaining a number of simulated scattered-radiation images from the plurality of initial images using a scatter model, the number of simulated scattered-radiation images being less than the plurality of initial images, wherein each simulated scattered-radiation image of the number of simulated scattered-radiation images is assigned one corresponding acquisition coordinate;

selecting images of the plurality of initial images that have respective acquisition coordinates equal to acquisition coordinates of the number of simulated scattered-radiation images; and training the neural network using the selected images as input data and the number of simulated scattered-radiation images as output data; and correcting each of the initial images using the corresponding scattered-radiation single image.

10. The method of claim 9, wherein the number of scattered-radiation images simulated for the training is increased automatically until a specified accuracy is achieved with regard to pixel values relating to the acquisition coordinates of adjacent scattered-radiation single images.

11. The method of claim 9, wherein a corrected three-dimensional (3D) image is reconstructed from the corrected initial images.

12. An imaging system comprising:

an imaging apparatus; and an image processing apparatus configured to train a neural network for correcting acquisitions obtained by the imaging apparatus, the image processing apparatus being configured to train the neural network comprising the image processing apparatus being configured to:

acquire a plurality of initial images at different acquisition coordinates using the imaging apparatus;

obtain a number of simulated scattered-radiation images from the plurality of initial images using a scatter model, the number of simulated scattered-radiation images being less than the plurality of initial images, wherein each simulated scattered-radiation image of the number of simulated scattered-radiation images is assigned one corresponding acquisition coordinate;

select images of the plurality of initial images that have respective acquisition coordinates equal to acquisition coordinates of the number of simulated scattered-radiation images; and train the neural network using the selected images as input data and the number of simulated scattered-radiation images as output data.

13. In a non-transitory computer-readable storage medium executable by a control facility of an imaging system to correct initial images obtained by radiation, the instructions comprising:

creating one scattered-radiation single image for each of the initial images using a neural network trained according to a method for training the neural network for correcting acquisitions obtained by an imaging apparatus, the method for training the neural network comprising:

acquiring a plurality of initial images at different acquisition coordinates using the imaging apparatus;

obtaining a number of simulated scattered-radiation images from the plurality of initial images using a scatter model, the number of simulated scattered-radiation images being less than the plurality of initial images, wherein each simulated scattered-radiation image of the number of simulated scattered-radiation images is assigned one corresponding acquisition coordinate;

selecting images of the plurality of initial images that have respective acquisition coordinates equal to acquisition coordinates of the number of simulated scattered-radiation images; and training the neural network using the selected images as input data and the number of simulated scattered-radiation images as output data; and correcting each of the initial images using the corresponding scattered-radiation single image.

14. The non-transitory computer-readable storage medium of claim 13, wherein the number of scattered-radiation images simulated for the training is increased automatically until a specified accuracy is achieved with regard to pixel values relating to the acquisition coordinates of adjacent scattered-radiation single images.

15. The non-transitory computer-readable storage medium of claim 13, wherein a corrected three-dimensional (3D) image is reconstructed from the corrected initial images.

* * * * *